United States Patent [19]

Hanefeld et al.

[11] Patent Number: 4,654,339
[45] Date of Patent: Mar. 31, 1987

[54] 3-AMINO-TETRAHYDRO-1,3-THIAZINE-2,4-DIONES, UTILIZATION THEREOF AND SKIN TREATING COMPOSITIONS CONTAINING SAID COMPOUNDS

[75] Inventors: Wolfgang Hanefeld, Marburg, Fed. Rep. of Germany; Rudi Röthlisberger, Marly; Friedrich Noser, Bonnefontaine, both of Switzerland

[73] Assignee: Wella Aktiengesellschaft, Darmstadt, Fed. Rep. of Germany

[21] Appl. No.: 662,308

[22] PCT Filed: Feb. 27, 1984

[86] PCT No.: PCT/EP84/00049
§ 371 Date: Oct. 9, 1984
§ 102(e) Date: Oct. 9, 1984

[87] PCT Pub. No.: WO84/03699
PCT Pub. Date: Sep. 27, 1984

[30] Foreign Application Priority Data

Mar. 16, 1983 [DE] Fed. Rep. of Germany ....... 3309400

[51] Int. Cl.$^4$ ................ A61K 31/54; A61K 7/06; C07D 279/04; C07D 417/04
[52] U.S. Cl. .................. 514/226; 540/467; 540/481; 540/470; 540/544; 540/553; 540/575; 540/597; 544/54; 514/852; 424/59; 424/64; 424/47
[58] Field of Search .............. 544/54, 55; 260/243.3; 424/246; 514/226; 540/467, 481, 470, 544, 553, 575, 597

[56] References Cited

U.S. PATENT DOCUMENTS 4,352,929 10/1982 Anderson et al. .................... 544/54

FOREIGN PATENT DOCUMENTS 516795 9/1955 Canada ................................. 544/54
2937184 4/1981 Fed. Rep. of Germany .

OTHER PUBLICATIONS

W. Hanefeld et al., Archiv der Pharmazie, Weinheim, 315(2) pp. 103–119 (1982).
CRC Handbook of Chemistry and Physics pp. C-1, C-2, C-8 and C-33–40 (60th Edition) CRC Press, Boca Raton Florida C(81).

Primary Examiner—John M. Ford
Attorney, Agent, or Firm—Michael J. Striker

[57] ABSTRACT

Novel 3-amino-tetrahydro-1,3-thiazine-2,4-diones as well as skin treating compositions on the basis of a physiologically compatible carrier and customary additions containing these novel 3-amino-tetrahydro-1,3-thiazin-2,4-dione derivatives as active ingredients for thickening the epidermis. The skin treating compositions are applied 1–2 times daily on the skin for about 3 to 4 weeks. Due to the thickening of the epidermis they cause a strengthening of the skin protection, in particular against sun rays, cold and the contact with harmful environmental substances of all kinds. Moreover, the skin treating compositions are suitable for prophylactically fighting the so-called ageing of skin.

25 Claims, No Drawings

3-AMINO-TETRAHYDRO-1,3-THIAZINE-2,4-DIONES, UTILIZATION THEREOF AND SKIN TREATING COMPOSITIONS CONTAINING SAID COMPOUNDS

The invention relates to 3-amino-tetrahydro-1,3-thiazin-2,4-diones as well as skin treating compositions containing said compounds.

The skin forms the limiting layer between the organism and its environment. Therefore, the most important task of the skin consists of protecting the inside of the body against exogenic influences. Our skin is in daily contact with substances wich are strange to the body and partially hostile to the body and in particular hostile to the skin. Particularly frequent contact of the unprotected skin with these substances, which very often are job related (hairdressers, dentists, housewives), sooner or later results in more or less damage to the skin. For preventing or at least for reducing such skin damage principally two types of intervention was hitherto used: a protective skin protection as well as a conserving skin care.

The protective skin protection consists in that the skin is treated before coming into contact with the strange i.e., foreign skin substance, so as to substantially exclude any direct contact between the skin surface and the damaging substances. The preparations which assure a protective skin protection effect, do so on a chemical-physical basis without interfering with the physiology of the skin. Such preparations must fulfill the following requirements: They should be impermeable and insoluble with respect to most of the exogenic harmful substances; they should have a good skin compatability; they should be easily applied to the skin surface and also easily removed therefrom; they should not interfere with the feel of the hands, so as not to interfere with the workability of the hands and should also have a certain prolonged period of effectiveness. The disadvantage of known preparations of this type is that they are not able to fullfill all these requirements to the optimum degree required.

It is an objective in the conserving skin care to make the skin less allergic when coming into contact with skin damaging substances. The protecting substances are already contained in the washing substances. Their efects differ in accordance with different types of skin protection measures sought and, which take effect effect by adsorption at the skin surface, lubricating measures, acidifying measures and deswelling measures. Here too, the essential disadvantage of these skin protective measures consists in that they are not effective in the same manner against attack by the different environmental harmful substances.

In contrast thereto, skin treating compositions containing a 3-amino-tetrahydro-1,3-thiazine-2,4-dione of the general formula I

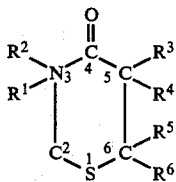

wherein $R^1$ and $R^2$ each represent H, alkyl, hydroxyalkyl, carboxyalkyl, halogenalkyl, cyanoalkyl, alkoxyalkyl, cycloalkyl, alkenyl, alkinyl, arylalkyl, arylalkyl substituted in the aryl moiety, aryl, alkyl-, halogen-, nitro-, alkoxy-, aryloxy-, cyano substituted aryl, acyl, thiazolyl, thienyl, benzthiazolyl, 1,3,4-thiadiaxolyl, oxazolyl, benzoxazolyl, 1,3,5-oxadiazolyl, pyrazolyl, 1,2,4-triazolyl, benzimidazolyl, pyridinyl, pyrimidinyl, purinyl, pyridazinyl, triazinyl, benzotriazinyl, quinolyl, isoquinolyl, cinnolinyl, phthalazolyl, pteridinyl, quinoxalinyl, acridinyl, or $R^1$ and $R^2$ taken together stand for alkylidene arylidene and heterocyclic-methylidene, wherein heterocyclic represents furan thiophene, pyrrole, pyridine, isozazole, thiazole, imidazole, 1,2,3-triazole, pyrazole, indole, benzthiazole, quinoline isoquinoline, quinoxaline, carbazole pteridine or where $R^1$ and $R^2$ together with the nitrogen atom, to which they are bound, are part of a herocyclic ring and in this ring represent the segment —$(CH_2)_n$—X—$(CH_2)_m$—, wherein X=$CH_2$, O, S, NR′ (R′=alkyl, arylalkyl, aryl), n=0 to 3 and m=1 to 3, provided that n is O, only when X=$CH_2$, $R^3$ represents H, alkyl, cycloalkyl, carboxyl, arylalkyl, aryl or substituted aryl, $R^4$ represents H, alkyl, cycloalkyl, arylalkyl, aryl or substituted aryl, $R^5$ is H, alkyl, substituted alkyl, cycloalkyl, arylalkyl, aryl, substituted aryl, 2-furyl or substituted 2-furyl, and $R^6$ represents H, alkyl, substituted alkyl, cycloalkyl, arylalkyl, aryl or substituted aryl, fullfill all requirements which are required from a skin protection preparation in view of its novel effectiveness.

Therefore, the subject matter of the described invention is skin treatment compositions containing physiologically compatible carriers, characterized by a content of at least one compound of the general formula I.

The skin treating compositions is accordance with the invention may be present in any given form of preparation suitable for skin treating compositions, for example, as a clear, colored or turbid solution, as a dispersion, emulsion, in form of a foam or as a preparation which can be sprayed from an aerosol container by means of a pump or by means of a propellent gas. Preferably, they are present in ointment, cream or gel form. Preparations, which may be considered in accordance with the invention are, for example, cosmetic skin treating compositions, such as day creams, night creams, nutritive creams, skin protection creams, sun protection creams, sun protection sprays, cold protection creams, as well as lipsticks, skin milk preparations, skin lotions and skin protection gels.

The concentration of the compounds of the general formula I amounts to about 0.1 to 5% by weight, preferably 0.5 to 3% by weight in the skin treating compositions. The compounds of formula I may be present alone or in a mixture in the composition.

The formulation of the skin treating composition constitutes a mixture of the compounds in accordance with formula I with physiologically compatible constituents, like carriers and admixed materials, i.e., adjuvants which are customary for such preparations.

Customary carriers and admixed materials in solutions, creams, emulsions or gels are, for example, solvents, as for example water, lower aliphatic alcohols, for example, ethanol, propanol and isopropanol, or glycols, such as glycerin and propylene glycol, furthermore netting agents or emulsifiers from the classes of the anionic, cationic, amphoteric or nonionogenic surface active substances, like fatty alcohol sulfates, alkyl sulfonates, alkyl benzene sulfonates, alkyl trimethyl ammonium salts, alkyl betaines, oxyethylated nonylphenols, fatty acid alkanolamides, oxyethylated fatty acid esters, furthermore thickeners, like higher fatty alcohols, fatty acid esters, starch, cellulose derivatives, Vaseline, stearin, ceresin, paraffin oil and fatty acids, as well as remedial substances, like lanolin, lanolin derivatives, cholesterin, pantothenic acid, sorbital, betaine, almond oil, avacado oil, bees wax and spermaceti.

Further customary admixed materials are, for example, cosmetic resins, dyes, perfume oils, propellent gases as well as preservatives, like, for example, p-hydroxybenzoic acid, sorbic acid, salicylic acid, formaldehyde and hexachlorophene. The compositions may contain bases, as, for example, triethanolamine for forming salts.

The manufacture of the skin treating compositions is carried out in the manner customary for such preparations in that the compounds of formula I, which serve a the active ingredient, are admixed with the constituents acting as carrier substances for the skin treating compositions and are then combined with the further constituents of the composition into a final product. The compounds of the general formula I which are contained in the skin treating composition described here cause following repeated topical applications a thickening of the outermost skin layer, namely of the dead keratin layer which, above all, is responsible for the natural skin protection. Due to the thickening of the keratin layer the skin becomes more resistant to any contact with environmental harmful substances, thereby providing an optimum skin protection in this manner. Since the skin protection, which is assured by these compounds, consists in that the natural skin protection is strengthened, the skin protection compositions in accordance with the invention, which contain the compounds in accordance with formula I, do not have the disadvantages which can be observed with conventional skin protection compositions. The skin treatment compositions in accordance with the invention may be applied independent of the time of the contact of the harmful substance with the skin surface. Hence, they never will intefere with an operating process, since they are no longer present on the skin surface at this point in time. The skin protection cannot be removed (for example, by washing), since it is obtained by the new condition of the skin (thickening). Simultaneously, the compounds of the general formula I effect a strengthening of the natural sun protection. This additional sun protection is also obtained by the thickening of the keratin layer which is obtained after the treatment with the skin treating composition in accordance with the invention. A thickening of the keratin layer causes an increased absorption of light or sun rays. This novel prophylactic sun protection (pre-sun) has clear advantages with respect to the efficiency obtained with the conventional sun protection compositions. The customary sun protection compositions are applied onto the skin surface and their absorption capacity, i.e., their ability provide light protection depends on the applied thickness of the layer. These preparations may interfere in that they are too oily, for example, thereby soiling the clothing. They will be rinsed off during bathing or showering, for example, and therefore must be reapplied. In contrast thereto, the compositions in accordance with the invention can be applied independent of the time of exposure the sun in that it can be applied repeatedly topically 3 to 4 weeks before starting a summer vacation, for example, so that it offers a long lasting protection, which cannot be washed off, against sunburn and other chronic light induced damage at the time of vacation thanks to the thickened keratin.

In a similar manner, the compositions in accordance with the invention which contain the 3-amino-tetrahydro-1,3-thiazine-2,4-diones of formula I, are able to provide a protection cold cold on exposed and sensitive body areas, for example, on the face and hands which are particularly exposed to poor weather conditions. Therefore, the compositions may be considered for use by skiers and high mountain athletes, for example, as a preventive protection against extreme cold. Thanks to their keratin thickening effect the skin treating compositions in accordance with the invention are able to offer an effective cold protection which does not have the uncomfortable side effects of the preparations which stress the skin and remain on the skin surface, because here too, it is merely a strengthening of the natural cold protection.

With increasing age, the outer layer of the skin, the so-called outer skin or epidermis, becomes thinner. The thinning of the epidermis is responsible for the skin's surface getting its parchment-like appearance, so that sebaceous glands, retention cysts, pigment spots as well as fine blood vessels become more visible, thus generating the typical condition of a so-called old skin. Since the compositions in accordance with the invention are able not only to thicken the keratin layer, which represents only a part of the epidermis, but is able to thicken the total epidermis, they represent an effective composition for a prophylactic treatment of skin aging.

Advantageously, the skin treating compositions in accordance with the invention should be used in such a manner that repeatedly and preferably 1 to 2 times a day the composition is applied to the corresponding skin areas about 2 to 3 weeks before a desired thickening of the keratin or the epidermis should be obtained.

The skin thickening effect of the compositions in accordance with the invention was demonstrated on hairless mice in the following manner:

2% by weight of the compounds a,e and h were topically applied to one side of the body of hairless mice (hr/hr) in form of a 50% by volume ethanolic solution over two and one half weeks every day, except Saturday and Sunday. At the end of the treatment time, the animals were killed and a 1×1.5 cm large piece of skin was removed from both body sides and histologically processed. The thickness of the upper skin was measured at about 100 locations and the average skin thickness was established. The thickening of the upper skin can be expressed as the quotient of the average thickness of the treated upper skin and the average thickness of the untreated skin. This quotient is stated as the thickening factor. The compounds in accordance with the invention resulted in thickening factors which were between 1.2 and 2.1.

The 3-amino-tetrahydro-1,3-thiazine-2,4-diones of formula I in accordance with the invention contained in the described skin treating compositions are novel.

Examples of novel compounds in accordance with the invention of formula I are
(a) 3-dimethylamino-5,5-diphenyl-tetrahydro-1,3-thiazine-2,4-dione
(b) 3-(N-acetyl-N-phenyl)-amino-5,5-diphenyl-tetrahydro-1,3-thiazine-2,4-dione (c) 3-[N-acetyl-N-(4-chlorphenyl)]-amino-5,5-diphenyl-tetrahydro-1,3-thiazine-2,4-dione
(d) 3-[N-acetyl-N-(4-nitrophenyl)]-amino-5,5-diphenyl-tetrahydro-1,3-thiazine-2,4-dione
(e) 3-diphenylamino-5,5-diphenyl-tetrahydro-1,3-thiazine-2,4-dione
(f) 3-dimethylamino-5,5-di-(4-tolyl)-tetrahydro-1,3-thiazine-2,4-dione
(g) 3-(1-perhydroazepinyl)-tetrahydro-1,3-thiazine-2,4-dione
(h) 3-(4-morpholinyl)-tetrahydro-1,3-thiazine-2,4-dione
(i) 3-(1-perhydroazepinyl)-5,5-di-(4-tolyl)-tetrahydro-1,3-thiazine-2,4-dione The manufacture of compounds of formula I is performed by oxidation of the corresponding 3-amino-tetrahydro-2-thioxo-1,3-thiazine-4-ones with chromic anhydride in acetic acid. The manufacture of these initial compounds is described in German laid open patent 2 937 184 as well as in the literature W Hanefeld et al., Archiv der Pharmazie, Weinheim, 315 (2) pages 103–119 (1982).

The process described there for making the 3-amino-4-oxo-2-thioxo-tetrahydro-1,3-thiazine of formula II consists in that hydrazine, a N-mono-substituted hydrazine, an N,N-disubstituted hydrazine, the salts of these compounds or hydrazones of aldehydes or ketones are reacted with dithiocarbazate in a suitable polar solvent, preferably in ethanol/pyridine, with carbon disulfide and a base, preferably soda lye, potash lye or a tertiary amine, subsequently reacting a β-lactone with to the salt of the dithiocarbazide acid-2-carboxy ethyl ester and after removing the solvent cyclizing the ester either by (A) by heating with acetanhydride and some drops of concentrated sulfuric acid directly to 3-amino-4-oxo-2-thioxotetrahydro-1,3-thiazine or (B) by adding hydrochloric acid transferring it to the free acid and then cyclizing it to the 3-amino-4-oxo-2-thioxo-tetrahydro-1,3-thiazine with acetanhydride/sulfuric acid.

The process is explained in more detail by the following reaction diagram wherein $R^1,R^2,R^3,R^4,R^5$ and $R^6$ have the aforementioned stated meanings:

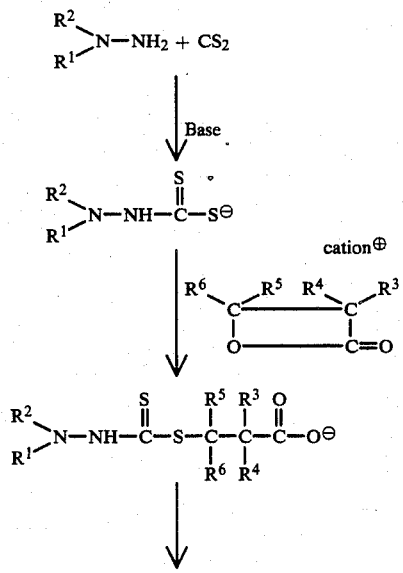

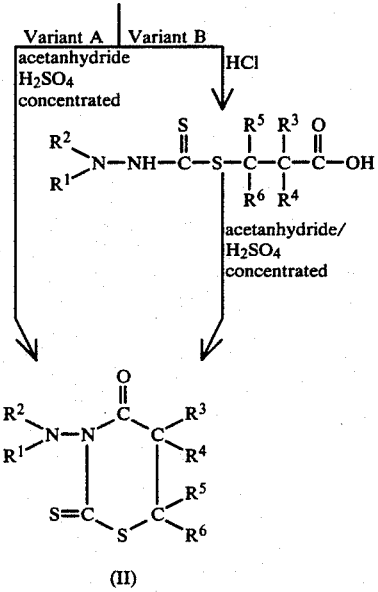

For manufacturing the 3-amino-tetrahydro-1,3-thiazine-2,4-diones in accordance with the invention of formula I, the corresponding 3-amino-tetrahydro-2-thioxo-1,3-thiazine-4-on of formula II is dissolved in 10 times of the amount by weight acetic acid and is reacted with 3 times the amount of Mol chromic acid anhydride in accordance the following reaction equation by heating for 1 to 2 hours under reflux to the desired product of formula I.

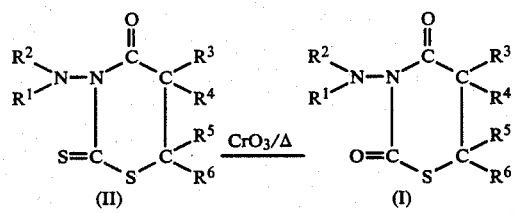

Subsequently, the reaction mixture is mixed with water until the start of turbidity and then cooled. The separated crystals of the 3-amino-tetrahydro-1,3-thiazine-2,4-dione are vacuumed off, washed with water, dried and subsequently recrystallized with a suitable solvent, for example, toluol, a mixture of acetone/water or diethyl ether/petroleum ether.

The following examples explain the subject matter of the invention in more detail.

EXAMPLES OF SKIN TREATING COMPOSITIONS

| Composition for skin protection |
|---|
| Lotion |
| 2.5 g 3-dimethylamino-5,5-diphenyl-tetrahydro-1,3-thiazine-2,4-dione |
| 3.5 g glycerin mono stearate, selfemulsifying |
| 2.0 g oleic acid |
| 5.0 g glycerin |
| 1.0 g triethanolamine |
| 5.0 g ethanol (96% by volume) |
| 0.3 g perfume and preservative |
| 80.7 g water |

-continued 100.0 g

Gel

- 3.0 g  3-[N—acetyl-N—(4-chlorphenyl)]-amino-5,5-diphenyl-tetrahydro-1,3-thiazine-2,4-dione
- 15.0 g  ethanol (96% by volume)
- 1.0 g  acrylic acid homopolymerisate
- 10.0 g  glycerin
- 0.8 g  triethanolamine
- 0.4 g  perfume and conserving composition
- 69.8 g  water 100.0 g

Pre-sun preparations (Sun protection compositions)

Lotion

- 2.0 g  3-diphenylamino-5,5-diphenyl-tetrahydro-1,3-thiazine-2,4-dione
- 3.0 g  glycerin mono stearate, self emulsifying
- 3.0 g  isopropylmyristate
- 2.0 g  glycerin
- 0.3 g  perfume and preservative
- 89.7 g  water 100.0 g

Emulsion

- 2.5 g  3-dimethylamino-5,5-diphenyl-tetrahydro-1,3-thiazine-2,4-dione
- 3.0 g  glycerin mono stearate
- 2.0 g  cetyl-stearyl alcohol (DAB 7)
- 1.5 g  cetyl-stearyl alcohol, with 12 Mol ethylene oxide oxethylized
- 1.5 g  cetyl-stearyl alcohol, with 20 Mol ethylene oxide oxethylized
- 0.5 g  hydrated castor oil
- 10.5 g  2-octyldodecanol
- 6.0 g  paraffin oil, viscous
- 0.4 g  perfume and conserving composition
- 72.6 g  water 100.0 g

Preparations for prophylactic cold protection

Milk

- 2.0 g  3-[N—acetyl-N—(4-nitrophenyl)]-amino-5,5-diphenyl-tetrahydro-1,3-thiazine-2,4-dione
- 5.8 g  sorbitanmonostearate
- 2.2 g  sorbitanmonooleate
- 8.0 g  almond oil
- 5.0 g  oleic acid decylester
- 3.0 g  2-octyldodecanol
- 6.0 g  perhydrosqualen
- 2.0 g  glycerin
- 1.8 g  propylene glycol
- 3.0 g  perfume and preservative
- 61.2 g  water 100.0 g

Gel

- 3.0 g  3-diphenylamino-5,5-diphenyltetrahydro-1,3-thiazine-2,4-dione
- 15.0 g  ethanol (96% by volume)
- 1.0 g  acrylic acid homopolymerizate
- 10.0 g  glycerin
- 0.8 g  triethanolamine
- 0.4 g  perfume and preservative
- 69.8 g  water 100.0 g

Preparations for prophylactic treatment of aged skin

Nutritive Cream

- 1.5 g  3-dimethylamino-5,5-diphenyl-tetrahydro-1,3-thiazine-2,4-dione
- 25.0 g  1:1 condensate of citric acid-di-stearyl ester and pentaerythrite-di-coconut oil acid ester
- 10.0 g  oleic acid decylester
- 10.0 g  isopropylmyristate
- 0.3 g  perfume and preservative
- 53.2 g  water 100.0 g

Antiwrinkle Cream

- 2.5 g  3-[N—acetyl-N—(4-chlorphenyl)]-amino-5,5-diphenyl-tetrahydro-1,3-thiazine-2,4-dione
- 7.0 g  glycerin mono palmitate distearate
- 7.0 g  stearic acid, three times pressed
- 1.5 g  jojoba oil
- 5.0 g  isoproylmyristate
- 2.0 g  glycerin
- 0.9 g  triethanolamine
- 3.0 g  perfume and preservative
- 71.7 g  water 100.0 g

EXAMPLES OF MANUFACTURE

Manufacture of 3-dimethylamino-5,5-diphenyl-tetrahydro-1,3-thiazine-2,4-dione (a):

6.85 g (20 mMol) 3-dimethylamino-5,5-diphenyl-2-thioxo-tetrahydro-1,3-thiazine-4-one are dissolved by heating in 7.0 g acetic acid and compounded with 6.0 g (60 mMol) $CrO_3$. After settling down of the violent exothermic reaction one heats up to the boiling point for one hour. One compounds with water until turbidity sets in and then the reaction mixture is cooled. The precipitated crystal are vacuumed off, washed off with water to a substantially colorless state and recrystallized with acetone/water. The physical data and analysis values can be seen in the following table.

For the remainder of the compositions of the general formula I in accordance with the invention (compositions a–i), the preparation of the corresponding 2-thioxo-composition is performed in an analogous manner as described above for composition (a). Depending on the substance (see table) one can use as a solvent for the recrystallization toluol, ethanol, diethyl ether/petroleum ether or diethyl ether/ethanol. The size of the individual charges were between 1.5 and 20 mMol.

The carbamoyl-C=O-band of the $C_2$ appears at 1660–1680 $cm^{-1}$ in the IR spectras of the compositions of formula I. The lactan-C=O-band of the $C_4$ can be observed at 1695–1730 $cm^{-1}$. The additional acetyl-C=O band occurs at 1740 $cm^{-1}$ in the compositions b to d.

TABLE 3-amino-tetrahydro-1,3-thiazine-2,4-diones in accordance with the invention of general formula I

| | $R^1$ | $R^2$ | $R^3$ | $R^4$ | $R^5,R^6$ | Melting point °C. (recrystallisation from) | Yield in theory | summation formula (Mol mass) | N calculated found | S calculated found |
|---|---|---|---|---|---|---|---|---|---|---|
| a | $CH_3$ | $CH_3$ | $C_6H_5$ | $C_6H_5$ | H | 195–200 (Aceton/Water) | 76 | $C_{18}H_{18}N_2O_2S$ (326.42) | 8.58 8.57 | 9.82 9.56 |
| b | $C_6H_5$ | $CH_3-\overset{\underset{\parallel}{O}}{C}$ | $C_6H_5$ | $C_6H_5$ | H | 178–181 (toluol) | 60 | $C_{24}H_{20}N_2O_3S$ (420.50) | 6.66 6.59 | 7.62 7.82 |

TABLE-continued 3-amino-tetrahydro-1,3-thiazine-2,4-diones in accordance with the invention of general formula I

| | $R^1$ | $R^2$ | $R^3$ | $R^4$ | $R^5, R^6$ | Melting point °C. (recrystallisation from) | Yield in theory | summation formula (Mol mass) | N calculated found | S calculated found |
|---|---|---|---|---|---|---|---|---|---|---|
| c | 4-Cl—$C_6H_4$ | $CH_3$—C(=O) | $C_6H_5$ | $C_6H_5$ | H | 177–179 (toluol) | 74 | $C_{24}H_{19}ClN_2O_3S$ (450.95) | 6.21 / 6.05 | 7.11 / 7.20 |
| d | 4-$NO_2$—$C_6H_4$ | $CH_3$—C(=O) | $C_6H_5$ | $C_6H_5$ | H | 198–199.5 (toluol) | 71 | $C_{24}H_{19}N_3O_5S$ (461.50) | 9.11 / 8.88 | 6.95 / 6.76 |
| e | $C_6H_5$ | $C_6H_5$ | $C_6H_5$ | $C_6H_5$ | H | 132–136 (toluol) | 71 | $C_{28}H_{22}N_2O_2S$ (450.56) | 6.22 / 6.02 | 7.12 / 7.32 |
| f | $CH_3$ | $CH_3$ | 4-$CH_3$—$C_6H_4$ | 4-$CH_3$—$C_6H_4$ | H | 190–192 (toluol) | 65 | $C_{20}H_{22}N_2O_2S$ (354.47) | 7.90 / 7.60 | 9.05 / 8.82 |
| g | —$(CH_2)_6$— | | H | H | H | 68–70 diethyl ether/petrol ether | 68 | $C_{10}H_{16}N_2O_2S$ (228.31) | 12.27 / 12.05 | 14.04 / 13.87 |
| h | —$(CH_2)_2$—O—$(CH_2)_2$— | | H | H | H | 112–114 ethanol/diethyl ester | 73 | $C_8H_{12}N_2O_3S$ (216.26) | 12.95 / 12.79 | 14.83 / 14.91 |
| i | —$(CH_2)_6$— | | 4-$CH_3$—$C_6H_4$ | 4-$CH_3$—$C_6H_4$ | H / H | 73–75 ethanol | 62 | $C_{24}H_{28}N_2O_2S$ (408.56) | 6.86 / 6.72 | 7.85 / 7.83 |

We claim:

1. A 3-amino-tetrahydro-1,3-thiazine-2,4-dione having the following formula:

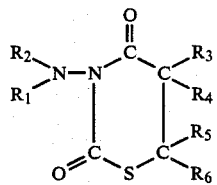

(I)

wherein $R^1$ and $R^2$ each represent H, Alkyl (C1–6), hydroxyalkyl (C1–6), carboxyalkyl (C1–6), halogenalkyl (C1–6), cyanoalkyl (C1–6), alkoxy (C1–6) alkyl (C1–6), cycloalkyl (C4–6), alkenyl (C2–6), alkinyl (C2–6), aryl (C3–10) alkyl (C1–6), aryl (C3–10) alkyl (C1–6) substituted in the aryl moiety, aryl (C3–10), aryl (C3–10) substituted with alkyl (C1–6), halogen, nitroalkoxy (1–6), aryloxy (C3–10) or cyano, acyl, thiazolyl, thienyl, benzthiazolyl, 1,3,4-thiadiazolyl, oxazolyl, benzoxazolyl, 1,3,5-oxadiazolyl, pyrazolyl, 1,2,4-triazolyl, benzimidazolyl, pyridinyl, pyrimidinyl, purinyl, pyridazinyl, triazinyl, benzotriazinyl, quinolyl, isoquinolyl, cinnolinyl, phthalazolyl, pteridinyl, quinoxalinyl, acridinyl or $R^1$ and $R^2$ taken together represents alkylidene, arylidene and heterocyclic-methylidene, wherein heterocyclic designates furan, thiophene, pyrrol, pyridine, isoxazole, thiazole, imidazole, 1,2,3-thiazole, pyrazole, indole, benzthiazole, quinoline, isoquinoline, quinoxaline or pteridine or $R^1$ and $R^2$ taken together with the nitrogen atom to which they are attached form part of a heterocyclic ring in which they designate the segment —$(CH_2)_n$—X—$(CH_2)_m$—, wherein X is $CH_2$, O, S, $NR^1$, wherein $R^1$ is alkyl (C1–6), aryl (C6–10) alkyl (C1–6), or aryl, n is 0 to 3, m is 1 to 3 provided that n is 2 only when X is $CH_2$, $R^3$ is H, alkyl (C1–6), cycloalkyl (C4–6), carboxyl, aryl (C3–10) alkyl (C1–6), aryl (C3–10) or aryl (C3–10) substituted with alkyl (C1–6), halogen, nitro, aryloxy (C3–10) or cyano, $R^4$ is H, alkyl (C1–6), cycloalkyl (C4–6) aryl (C3–10) alkyl (C1–6) or aryl (C3–10) substituted with alkyl (C1–6), halogen, nitro, aryloxy (C3–10) or cyano, $R^5$ is H, alkyl (C1–6), alkyl (C1–6) substituted with halogen, nitro, aryloxy (C3–10) or cyano, cycloalkyl (C4–6), aryl (C3–10) alkyl (C1–6), aryl (C3–10), aryl (C3–10) substituted with alkyl (C1–6), halogen, nitro, aryloxy (C3–10) or cyano, 2-furyl or 2-furyl substituted with alkyl (C1–6), halogen, nitro, aryloxy (C3–10) or cyano, and $R^6$ is H, alkyl (C1–6), alkyl (C1–6) substituted with halogen, nitro, aryloxy (C3–10) or cyano, cycloalkyl (C4–6), aryl (C3–10) alkyl (C1–6) or aryl (C3–10) substituted with alkyl (C1–6), halogen, nitro, aryloxy (C3–10) or cyano.

2. A 3-amino-tetrahydro-1,3-thiazine-2,4-dione according to claim 1 designated 3-dimethylamino-5,5-diphenyl-tetrahydro-1,3-thiazine-2,4-dione.

3. A 3-amino-tetrahydro-1,3-thiazine-2,4-dione according to claim 1 designated 3-(N-acetyl-N-phenyl)-amino-5,5-diphenyl-tetrahydro-1,3-thiazine-2,4-dione.

4. A 3-amino-tetrahydro-1,3-thiazine-2,4-dione according to claim 1 designated 3-[N-acetyl-N-(4-chlorphenyl)]-amino-5,5-diphenyl-tetrahydro-1,3-thiazine-2,4-dione.

5. A 3-amino-tetrahydro-1,3-thiazine-2,4-dione according to claim 1 designated 3-[N-acetyl-N-(4-nitrophenyl)]-amino-5,5-diphenyl-tetrahydro-1,3-thiazine-2,4-dione.

6. A 3-amino-tetrahydro-1,3-thiazine-2,4-dione according to claim 1 designated 3-diphenylamino-5,5-diphenyl-tetrahydro-1,3-thiazine-2,4-dione.

7. A 3-amino-tetrahydro-1,3-thiazine-2,4-dione according to claim 1 designated 3-dimethylamino-5,5-di-(4-tolyl)-tetrahydro-1,3-thiazine-2,4-dione.

8. A 3-amino-tetrahydro-1,3-thiazine-2,4-dione according to claim 1 designated 3-(1-perhydroazepinyl)-tetrahydro-1,3-thiazine-2,4-dione.

9. A 3-amino-tetrahydro-1,3-thiazine-2,4-dione according to claim 1 designated 3-(4-morpholinyl)-tetrahydro-1,3-thiazine-2,4-dione.

10. A 3-amino-tetrahydro-1,3-thiazine-2,4-dione according to claim 1 designated 3-(1-perhydroazepinyl)-5,5-di-(4-tolyl)-tetrahydro-1,3-thiazine-2,4-dione.

11. A composition for treating skin to effect a thickening of the skin's outer layers and strengthening thereof to provide increased protection comprising a physiologically acceptable carrier and an effective amount of at least one compound according to claim 1.

12. A composition according to claim 11 wherein said compound is present in an amount of 0.1 to 5 by weight.

13. A composition according to claim 11 wherein said compound is present in an amount of 0.5 to 3% by weight.

14. A composition according to claim 11 containing at least one other material selected from the group consisting of water, lower alkanols, glycols, emulsifiers, surface active agents, thickening agents, lubricating agents, cosmetic resins, cosmetic dyes, perfume oils, preservatives, salt forming agents, and propellant gases.

15. A composition according to claim 11 in gel form.

16. A composition according to claim 11 in lotion form.

17. A composition according to claim 11 in the form of a cream.

18. Method of protecting skin from exposure to irritants and toxic or harmful substances in the atmosphere which comprises applying a composition according to claim 11 topically onto the skin 1 to 4 times a day for 2 to 4 weeks.

19. Method of protecting skin from exposure to cold which comprises applying a composition according to claim 11 topically onto the skin 1 to 4 times a day for 2 to 4 weeks.

20. Method of protecting skin from exposure to sunrays which comprises applying a composition according to claim 11 topically onto the skin 1 to 4 times a day for 2 to 4 weeks.

21. Method of protecting skin so as to inhibit the appearance of signs of aging which comprises applying a composition according to claim 11 topically onto the skin 1 to 4 times a day for 2 to 4 weeks.

22. A composition for treating skin in accordance with claim 11 wherein said composition is a skin protection composition.

23. A composition for treating skin in accordance with claim 11 wherein said composition provides protection on exposure to the sun.

24. A composition for treating skin in accordance with claim 11 wherein said composition provides protection on exposure to cold.

25. A composition for treating skin in accordance with claim 11 wherein said composition provides protection against the effects of aging.

* * * * *